United States Patent [19]
Stevens

[11] Patent Number: 5,972,143
[45] Date of Patent: *Oct. 26, 1999

[54] ANGIOGRAPHIC CATHETER WITH UNITARY BODY AND TIP SECTIONS AND METHOD FOR MAKING SAME FROM A CONTINUOUS FEEDSTOCK

[76] Inventor: Robert C. Stevens, P.O. Box 250, Williston, Fla. 32696

[ * ] Notice: This patent is subject to a terminal disclaimer.

[21] Appl. No.: 08/965,776

[22] Filed: Nov. 7, 1997

Related U.S. Application Data

[63] Continuation-in-part of application No. 08/747,360, Nov. 12, 1996, Pat. No. 5,738,742.

[51] Int. Cl.⁶ ............................. A61M 25/00; B32B 1/10
[52] U.S. Cl. ................... 156/149; 156/154; 156/244.12; 156/244.14
[58] Field of Search .................................... 156/149, 154, 156/155, 244.12, 244.14; 264/103, 171.26, 171.27, 139; 604/282

[56] References Cited

U.S. PATENT DOCUMENTS

| | | | |
|---|---|---|---|
| 3,485,234 | 12/1969 | Stevens | 604/282 |
| 3,585,707 | 6/1971 | Stevens | 264/103 |
| 3,720,235 | 3/1973 | Schrock | 138/137 |
| 3,945,867 | 3/1976 | Heller, Jr. et al. | |
| 3,988,189 | 10/1976 | Sullivan | |
| 4,321,226 | 3/1982 | Markling | 264/171.26 |
| 4,577,543 | 3/1986 | Wilson | 604/282 |
| 4,904,431 | 2/1990 | O'Maleki | 156/149 |
| 5,135,516 | 8/1992 | Sahatjian | 604/265 |
| 5,244,619 | 9/1993 | Burnham | 264/209.4 |
| 5,514,236 | 5/1996 | Avellanet et al. | 156/149 |
| 5,560,103 | 10/1996 | Harris et al. | 156/154 |
| 5,667,499 | 9/1997 | Welch | 138/125 |
| 5,702,373 | 12/1997 | Samson | 604/282 |

FOREIGN PATENT DOCUMENTS

| | | |
|---|---|---|
| 2454907 | 11/1980 | European Pat. Off. |
| 0086498 | 8/1983 | European Pat. Off. |

*Primary Examiner*—Daniel Stemmer
*Attorney, Agent, or Firm*—Fay, Sharpe, Beall, Fagan, Minnich & McKee, LLP

[57] ABSTRACT

A method of manufacturing angiographic catheters comprises providing a length of elastomeric tube of a predetermined outer diameter and braiding multiple strands of wire wrapping about its exterior. A plastic bonding agent is extruded onto the entire length of the wire wrapping to bond the strands to each other. Thereafter, the wire wrapping is ground away at predetermined spaced locations along the length of the elastomeric tube to provide a series of wire wrapped sections joined by non-wrapped sections. An elastomer layer is disposed over both the wire wrapped sections and the non-wrapped sections throughout the length thereof. Subsequently, the coated length is severed into pieces with the pieces each constituting unitary construction including a wire wrapped section that forms a catheter body and a non-wrapped section joined to at least one end thereof to constitute a flexible catheter tip.

38 Claims, 6 Drawing Sheets

ANGIOGRAPHIC CATHETER WITH UNITARY BODY AND TIP SECTIONS AND METHOD FOR MAKING SAME FROM A CONTINUOUS FEEDSTOCK

CROSS-REFERENCE TO RELATED APPLICATIONS

This is a continuation-in-part of my co-pending application Ser. No. 08/747,360 filed Nov. 12, 1996, now U.S. Pat. No. 5,738,742, entitled "Method of Making an Angiographic Catheter."

BACKGROUND OF THE INVENTION

The subject invention is directed toward the art of angiographic catheters and to catheter manufacturing methods and, more particularly, to a catheter having an improved unitary construction and to an improved method for manufacturing multiples of such catheters from a continuous feedstock.

Angiographic catheters are used for diagnostic purposes as well as for angioplasty. It is generally agreed that a good catheter should have the following features:

a) torsion control with a 1:1 rotation about its central longitudinal axis even when subjected to curvatures of as much as 110° along the catheter's length;

b) the ability to withstand high injection pressures of as much as 1000 PSI which are required where large amounts of contrast media is needed to properly visualize a given area to be studied;

c) push ability in conjunction with good torsional control along its axis mandates a catheter body having a controlled rigidity since if too rigid, it can cause injury and if too flexible, it may buckle;

d) a controlled degree of flexibility at the catheter tip is necessary to prevent injury to vessel openings and to vessel walls and this can be accomplished by using a softer plastic in this region, annular grooving, or decreasing the diameter as compared to the catheter body; and, e) the catheter tip must be easily formed and must retain the formed shape even when subjected to straightening when passed over a guide wire.

A catheter with the above features is described in my prior U.S. Pat. No. 3,485,234, which issued Dec. 23, 1969. My prior U.S. Pat. No. 3,585,707, which issued Jun. 22, 1971, sets forth how to make or manufacture the catheter.

The catheter construction described in these prior patents uses a wire braid reinforcing to provide torsional control and to strengthen the catheter body to better withstand high pressure injections. In order to have a flexible tip with good shape memory, it is necessary that no wire braid be in the tip area. The earlier patents describe the manner in which a tip portion is added to the catheter body. The tip portion, without braid, is formed as a separate item and is molded or fused to the end of the catheter body. This has been the weakest portion of the catheter, since the tip may become loosened or separated over a period of time or from physical abuse such as using an oversized guide wire, severe twisting or attempts at re-shaping the curvature of the tip.

The original manufacturing process used for making the original older catheters of the type described above is generally set forth in the flow chart of FIG. 1. In particular, the process involves the following steps (the paragraph numbers correspond to the sequence numbers shown in FIG. 1):

1) The process starts by forming a length of elastomeric tube. The tube is formed by starting with a silver plated copper wire or a monofilament of plastic (such as "Celcon" manufactured by the Hoechst Celanese Corporation, or Ultraform, an acetal copolymer manufactured by BASF), of a diameter equal to the published lumen diameter of the catheter being manufactured. This wire or monofilament is referred to as the "mandrel." As an example, a standard French 7 catheter has a lumen of 0.046 inches and an outside diameter of 0.092 inch. The wire or monofilament is purchased and used in continuous lengths of over 5000 feet. This wire or monofilament is referred to as a "mandrel" because the catheter is built on it.

The mandrel is passed through a plastic extruder, coating the mandrel with the selected elastomer to approximately 0.006 inch wall thickness. The elastomer or plastic used, for example, could be polyurethane containing bismuth or barium to make it opaque to x-rays, or radiopaque.

2) The coated mandrel is then placed in a "braiding machine" which overlays the elastomeric tube extrusion with multiple (e.g., 16) strands of 0.003 inch or smaller diameter stainless steel wire.

3) After the entire length of elastomeric extrusion has been overlaid with the wire braid, it is then cleaned in an ultrasonic cleaning bath and again passed through the plastic extruder adding another layer of plastic creating a wall thickness of approximately 0.012 inch. The combined layers of plastic and wire braid on the 0.046 inch diameter mandrel will now be approximately 0.094 inch in diameter.

4) Catheter tip material requires only a single extrusion on a corresponding mandrel wire because no braiding is required. The single layer of plastic applied to a 0.046 inch mandrel will have a wall thickness of 0.024 inch for a total diameter of 0.094 inch.

5) The body material and the tip material is cut to lengths of approximately 42 inches. This mandrel is now removed from within the cut lengths of body and tip material. This is done by stretching the mandrel, if necessary, to reduce its diameter and facilitate its withdrawal from within the plastic extrusion.

6) This material is then passed through a centerless grinder and ground to the proper diameter size and to a fine, smooth surface.

7) The tip material is then cut to lengths of approximately 3½ inches and tapers are ground on one end where necessary and a flare is formed at the other end.

8) The body material is ground to a taper at one end to mate with the internal taper of the flared tip portion.

9) A steel rod approximately 0.044 inch diameter is inserted into a catheter body and a tip is slipped onto the rod and the external taper of the body is mated with the internal taper of the tip.

10) Next, a sleeve or tube of Teflon about 6 inches in length is passed over the tip-body mated section. The tip-body with the Teflon sleeve are then pressed through a die that has been heated to approximately 325° F. The heat plus the pressure of the sleeve fuses and mold the joined sections by melting the plastic of both parts into a smooth joint. Where necessary, the catheter assembly is again passed through the centerless grinder, particularly if the fused joint is slightly larger than the rest of the catheter. It is important that the catheter with tip be within + or −0.001 inch of the published diameter.

11) The finished catheter is cut to the published length, a luer hub is added to the proximal end and the tip portion is then shaped with a forming wire in boiling water. The shapes of catheter tips are many, such as a single curve, double curve, Judkins left, Judkins right, pigtail, etc.

One major problem with the original construction of these earlier catheters is that it has been necessary to mold or fuse the tip by hand. This is very labor intensive and, therefore, expensive. In an age of rising medical costs, it is even more important than ever to reduce manufacturing costs.

My earlier related co-pending application teaches a novel catheter construction and a method which eliminates the need to manually mold or fuse the tip to thereby allow the catheter to be made as a single, unitary construction. All of the good features of the original catheter construction have been preserved in the method and apparatus of my earlier application including the wire braid in the body of the catheter and the absence or lack of wire braid in the tip area. The method of my earlier application is fully automated, eliminating the hand crafting of the catheter tip. This makes the catheter taught there safer and less expensive to manufacture than the original early styles.

In accordance with my earlier co-pending application and with reference now to FIGS. 2a–2f, the method of manufacturing angiographic catheters, each having an overall length L, generally comprises forming a length of cylindrical elastomeric tube 10 of a predetermined outer diameter (FIG. 2a) and braiding multiple strands of fine stainless steel wire wrapping about the elastomeric tube, forming a braided tube construction 12 shown in FIG. 2b. Thereafter, a bonding agent or adhesive is applied to the braided construction circumferentially thereof at spaced locations 14, 16 and 18 as showl in FIG. 2c causing the strands of wire wrapping to be bonded to each other and to the elastomer. Subsequent to the bonding, predetermined sections of the wire wrapping are removed from the elastomeric tube to leave a length of elastomeric tube with multiple wire wrapped sections 20, 22, 24 and 26 spaced from one another by unwrapped sections 30, 32 and 34 such that each wire wrapped section 20, 22, 24 and 26 has axially spaced ends enclosed by the bonding agent (e.g., wire wrapped section 22 has axial spaced ends at the unwrapped sections 30, 32) to prevent loosening or unwinding of the wire wrapping as best shown in FIG. 2d. A continuous layer of an elastomer is coated over the length of the elastomeric tube with multiple wire-wrapped sections to produce a uniform diameter length 36 of elastomeric coated wire-wrapped sections spaced apart from one another by unwrapped sections as shown in FIG. 2e. The continuous length thus produced is thereafter cut transversely at locations selected to reduce the length to multiple pieces of coated wire-wrapped sections having length L, each having a coated, unwrapped section joined thereto on at least one end thereof forming a catheter 38 having a preferred unitary construction as shown in FIG. 2f.

The manufacturing method described in my earlier filed co-pending application and briefly here is substantially more efficient than the original prior art methods described above in this specification and produces catheters having superior characteristics over the original prior art devices. However, the steps required to apply the bonding agent or adhesive at the various spaced-apart locations have proven to be somewhat of a time constraint in the manufacturing process. In that regard, the adhesive requires a cure time before the grinding process can begin. Even through the use of heat or UV curing, the drying cycle takes a finite amount of time. Also, the starting and stopping of the longitudinal motion of the mandrel first at each elastomeric layer site and then at each grinding section site spaced apart by a length L is somewhat time consuming and produces undesirable wear and tear on the catheter manufacturing apparatus.

It would therefore be desirable to manufacture multiple catheters from a single feedstock using a continuous process of depositing a uniform layer of a bonding agent directly onto the wire braiding. In order to reduce manufacturing cycle time, it would be desirable to deposit the bonding agent onto the entire length of feedstock covered with the wire braiding in a single manufacturing operation. It would further be desirable to deposit the bonding agent directly onto the wire braiding using an extrusion process.

SUMMARY OF THE INVENTION

The subject invention greatly simplifies the process of forming the catheters according to my earlier application by eliminating one of the above-described discontinuous steps. The step of applying the bonding agent or adhesive onto the wire wrapping circumferentially thereof at spaced locations has been replaced in the instant application with an extrusion process for uniformly coating the wire wrapping with a continuous layer of a plastic bonding agent. In addition, the process is not only simplified, but also results in a significantly better product having a unitary construction. In particular, and in accordance with the subject invention, the method of manufacturing angiographic catheters generally comprises forming a length of cylindrical elastomeric or plastic base tube of a predetermined outer diameter and braiding multiple strands of wire wrapping about the base tube. Thereafter, a thin layer of a plastic bonding agent is extruded onto the wire wrapping along the length of the base tube to cause the strands of wire wrapping to be bonded to each other and to the elastomer or plastic forming the base tube. Subsequent to the bonding, predetermined sections of the wire wrapping are removed from the base tube to leave the length of tube with multiple wire wrapped sections spaced from one another by unwrapped sections. Each wire wrapped section is encased by the bonding agent and has axially spaced ends enclosed by the layer of the plastic bonding agent to prevent loosening or unwinding of the wire wrapping. Over the length of the elastomeric tube with the multiple wire wrapped sections, there is then coated a continuous layer of elastomer to produce a uniform diameter length of elastomeric coated wire wrapped sections spaced from one another by unwrapped sections. The continuous length thus produced is thereafter cut transversely at locations selected to reduce the length to multiple pieces of coated wire wrapped sections each having a coated unwrapped section joined thereto at least one end thereof. The wire wrapped section of this length forms the main length and body of the catheter while the unwrapped section forms a continuous integral tip for the catheter. The tip section can, of course, be further treated to taper same and/or shape same to a desired shape. The method thus forms the main body of the catheter and the tip as a unitary structure eliminating the previously-required separate formation of the two elements following by the labor-intensive forming and bonding necessary in the prior art process.

The method also forms a catheter with a body section having a more uniform cross-section than the catheter described in my earlier co-pending application. In the earlier design, the bonding agent was applied to the wire wrapping only at spaced locations along the length of the elastomeric tube, resulting in at least one pair of layering discontinuity along the length of the catheter body near the tip. The method herein produces a catheter without one of the layering discontinuities.

It is also contemplated that the coating of the continuous layer of elastomer over the length of elastomeric tube with the multiple wire wrapped sections will be accomplished by a conventional extruding operation.

It should be appreciated that there may be variations of the basic inventive process. The actual length in which the components are produced can also vary widely. Similarly, the orientation of the individual sections that are subsequently cut into separate and individual catheters can, of course, be varied and the types of elastomers used at various times during the process can differ.

As can be seen from the foregoing, a primary object of the invention is the provision of a simplified process for forming multiple angiographic catheters from a continuous feedstock.

A still further object of the invention is the provision of a method of the general type described wherein the main body of the catheter and its associated tip are formed integrally and of a unitary construction to eliminate numerous bonding and finishing steps required by the prior art processes.

Yet another object of the invention is the provision of a process of the type described wherein the processing can be accomplished with conventional well known types of grinding, braiding, and extruding machinery.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof, and wherein.

DETAILED DESCRIPTION OF THE PREFERRED EMBODIMENT

Figure 1:
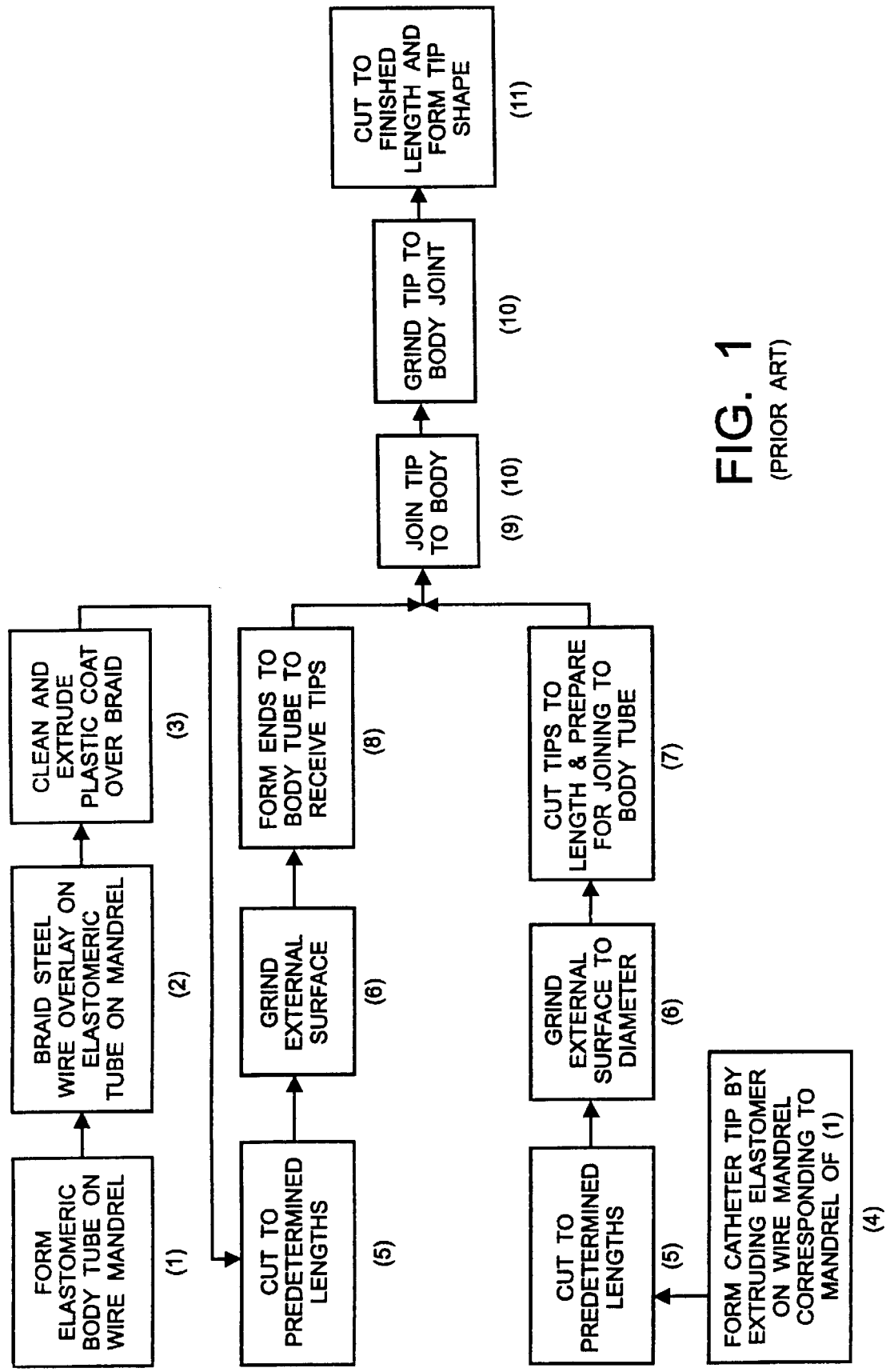
FIG. 1 is a flow chart showing a typical prior art processing method used for forming angiographic catheters.
Figure 2A:
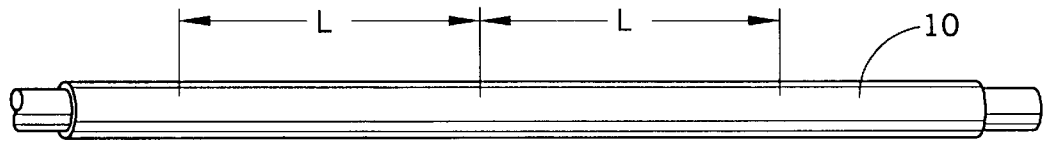
FIGS. 2a–2e are views in side elevation of the catheter of my prior co-pending application shown in various stages of sequential construction.
Figure 2B:
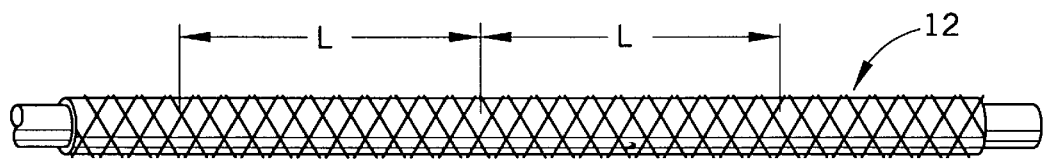
Figure 2C:
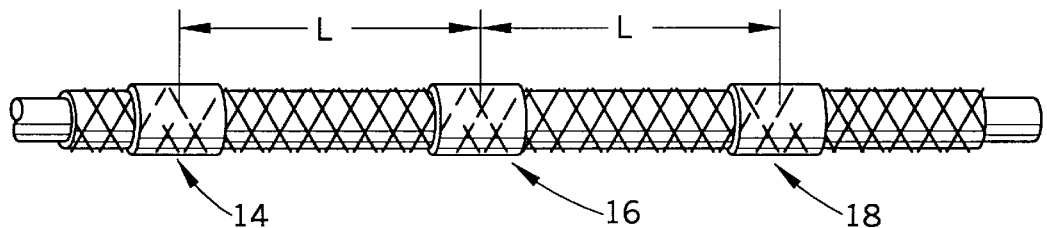
Figure 2D:
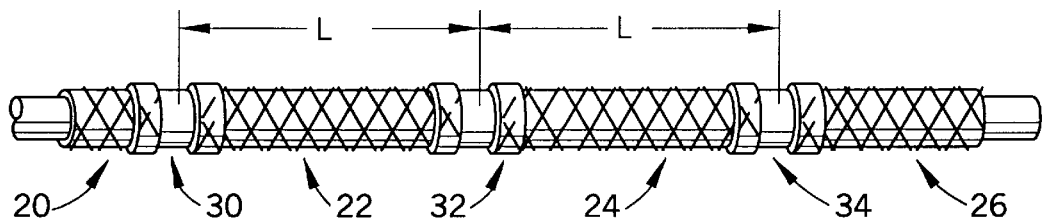
Figure 2E:
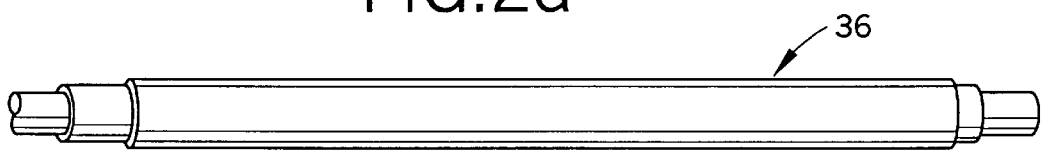
Figure 2F:
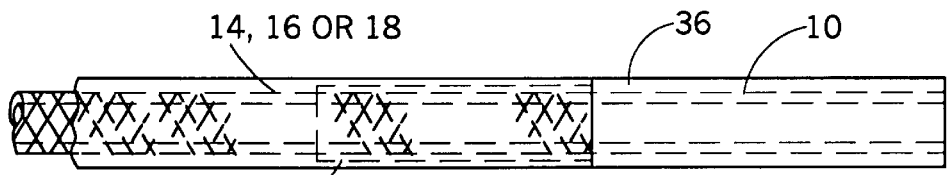
FIG. 2f is a view, partially in section, of the catheter of my prior co-pending application illustrating the internal construction of the catheter tip area.
Figure 3:
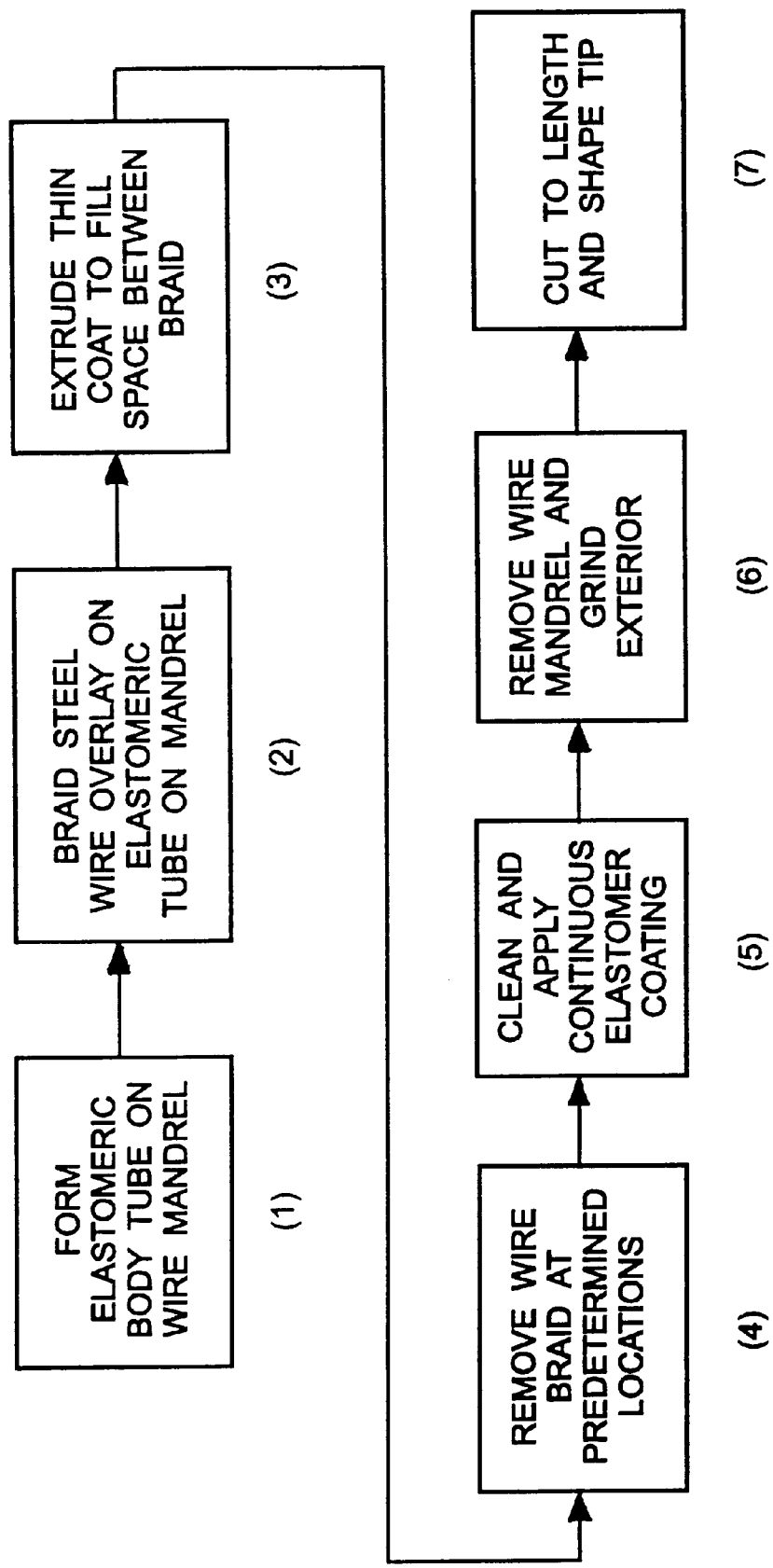
FIG. 3 is a process chart similar to FIG. 1 but showing the preferred processing steps according to the invention.
Figure 4A:
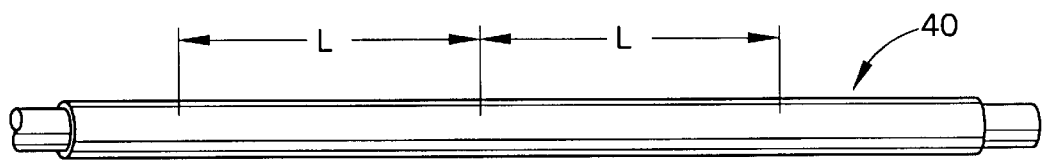
FIGS. 4a–4e are views in side elevation of multiple catheters formed in accordance with the present invention from a continuous feedstock shown in various stages of sequential construction.

Referring now to the drawings wherein the showings are for the purposes of illustrating the preferred embodiment of the invention only and not for purposes of limiting same, in FIG. 3, the full sequence of steps for the preferred embodiment of the inventive process are set forth in relative diagrammatic form. The side elevational views of the catheter shown in FIGS. 4a–4f in various stages of construction correspond with the manufacturing method steps illustrated in FIG. 3. It will be noted in comparing FIG. 3 to the prior art manufacturing process shown in FIG. 1 and previously described above that there is no separate sequence of steps required to form tip sections. Rather, the entire sequence of steps involves a progressive processing of what is basically a single element. In particular, as shown in FIG. 3, the process begins by the formation of an elastomeric tube 40 (FIG. 4a) that has an internal open diameter that corresponds to the desired internal diameter equal to the lumen diameter of the catheter to be made. As an example, for a "French 7" size, the lumen diameter is 0.046 inches. The elastomeric body tube could be formed in other ways, but in the preferred form of the invention, it is formed by extruding a desired elastomeric material such as a relatively soft polyurethane onto a wire mandrel or onto a monofilament mandrel made of a suitable plastic having the desired lumen diameter. In the preferred embodiment illustrated, the mandrel is formed of silver plated copper.

One material that has been found to be particularly well suited for use as a catheter tube body is Pellethane, a urethane produced by Dow Chemical. In addition, other materials have been found to be adequately well suited such as nylon materials including PEBAX available from Dow Chemical. The wire can be in substantially any desired length, but is preferably a substantial number of multiples of the desired final length of the catheter being formed. As an example, I have found that it is advantageous to construct multiple catheter tube bodies onto a continuous reel of five thousand (5,000) feet of mandrel feedstock. For catheters having a nominal length of forty two (42) inches, the present invention yields up to 1,250 catheters from a single roll of feedstock.

Figure 4B:
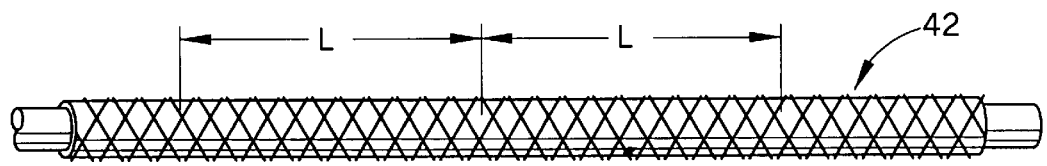

According to the preferred manufacturing method, the entire length, preferably five thousand (5,000) feet, of wire or monofilament which is to function as the mandrel in the formation of the basic elastomeric body tube is passed through a conventional extruder to coat the mandrel with a selected thickness, preferably of 0.006 inches, of elastomer which would vary depending upon the size of the catheter being made. Thereafter, the elastomeric tube 40 (FIG. 4a), preferably the entire five thousand (5,000) foot length, with the mandrel in place, is passed through a conventional braiding machine which overlies the elastomeric body tube with multiple strands of a small diameter stainless steel wire to form a composite braided structure 42 (FIG. 4b). For example, it is common to use 16 strands of 0.003 inch diameter stainless steel wire which is braided onto the elastomeric body tube in the manner discussed in my prior U.S. Pat. No. 3,585,707 which is incorporated herein by reference.

Figure 4C:
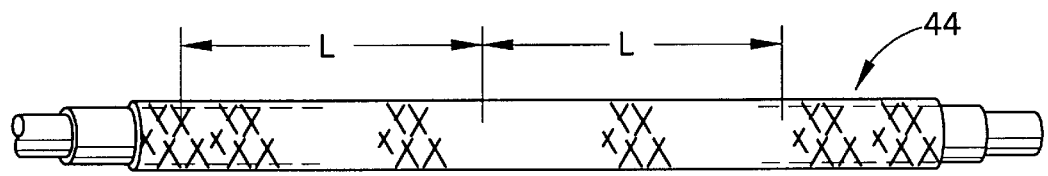
Figure 4D:
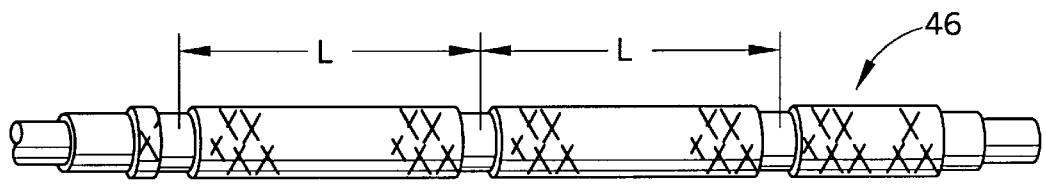

Thereafter, the entire length, in the preferred embodiment illustrated five thousand (5,000) feet, of the braided overlay is coated with a suitable coating capable of bonding the wire elements on the braided body together. This forms a coated braided composite structure 44 (FIG. 4c). Epoxy coatings have been used for this purpose as well as coatings that are UV curable. However, those coatings must be applied with rollers, brushed on, or sprayed. It is important that only enough epoxy or other adhesives be applied to fill the interstices of the wire braid and onto the base coating. This is hard to control using coatings. In the preferred form according to the present invention therefore, the coating for bonding the braid to the body tube is extruded onto the entire length of the feedstock carrying the elastomeric body tube with the braided overlay.

According to the present invention the coating is preferably a plastic material such as Pellethane which is a urethane produced by Dow Chemical. Alternatively, however, a nylon material can be used such as PEBAX. I have found that the thermal properties of these materials enable them to be extruded, one plastic upon another plastic, without the first plastic layer being scraped away in the guider tip of the extruder nozzle. In that manner, the entire base coat comprising the catheter tube body is extrudable through the extruder tip for the formation of a second layer of plastic extrusion directly onto the braided catheter body tube. In the preferred embodiment, the secondary layer of plastic extrusion material is formed to a thickness of 0.003 inches upon the braided overlay. Although the secondary plastic coating is thin, it penetrates between the strands of wire braid and mechanically locks the stainless steel wires in place so that they do not unravel during the grinding operation described below.

Subsequent to the plastic or epoxy coating in the manner described above, the length of braided and epoxy coated stock is treated so as to remove approximately 3½ inches (length of soft tip portion) of braided material every 42 inches (overall length of catheter) for the entire length of feedstock. This forms a composite cylindrical tube 46 (FIG. 4*d*) with multiple wire wrapped sections spaced from one another by unwrapped sections. The plastic or epoxy holds the remaining braided sections in place and prevents unraveling. Preferably, and in accordance with the preferred embodiment, the braid is removed by a grinding operation. The depth of the grind is approximately 0.006 inch so that the braiding is removed down to the base coat which is the formed elastomeric tube formed in the first step. The present invention is adapted to construct catheters having any overall length by merely spacing apart the ground area by more or less than 42 inches. In addition, various catheter tip lengths are constructed by grinding more or less than 3½ inch areas of wire braid.

Centerless grinders are widely used in industry and in angiographic catheter manufacture in particular. Catheter stock is "fed" though the grinder to remove excess plastic and to bring it to an accurate diameter. The grinder also creates a smooth surface finish. Centerless grinders are also used to grind tapers on catheter tips.

In centerless grinding, the machine weighs over 1000 pounds. This helps to give it great accuracy (+ or –0.0001 inch). The grinding wheel used in catheter production can be 6–8 inches in diameter with a width of 4 inches or greater. Perfect balancing is mandatory.

In centerless grinding, the part to be ground must be rotated under the grinding wheel. This is not a problem where the part is inches or even a few feet in length. However, where the part to be ground is 5000 feet or longer, this is not very satisfactory. With 5000 feet of braided catheter material on a spool weighing 50 pounds or more, it is not generally practical to rotate the spool at speeds of at least 200 RPM. Not only would you have to rotate the spool, but also feed off sections of braided material every 42 inches as you rotate.

In order to rotate the catheter stock during grinding and use the standard heavy but accurate centerless grinders currently available, I have devised a means to rotate only the portion of the catheter stock to be ground.

Figure 5:
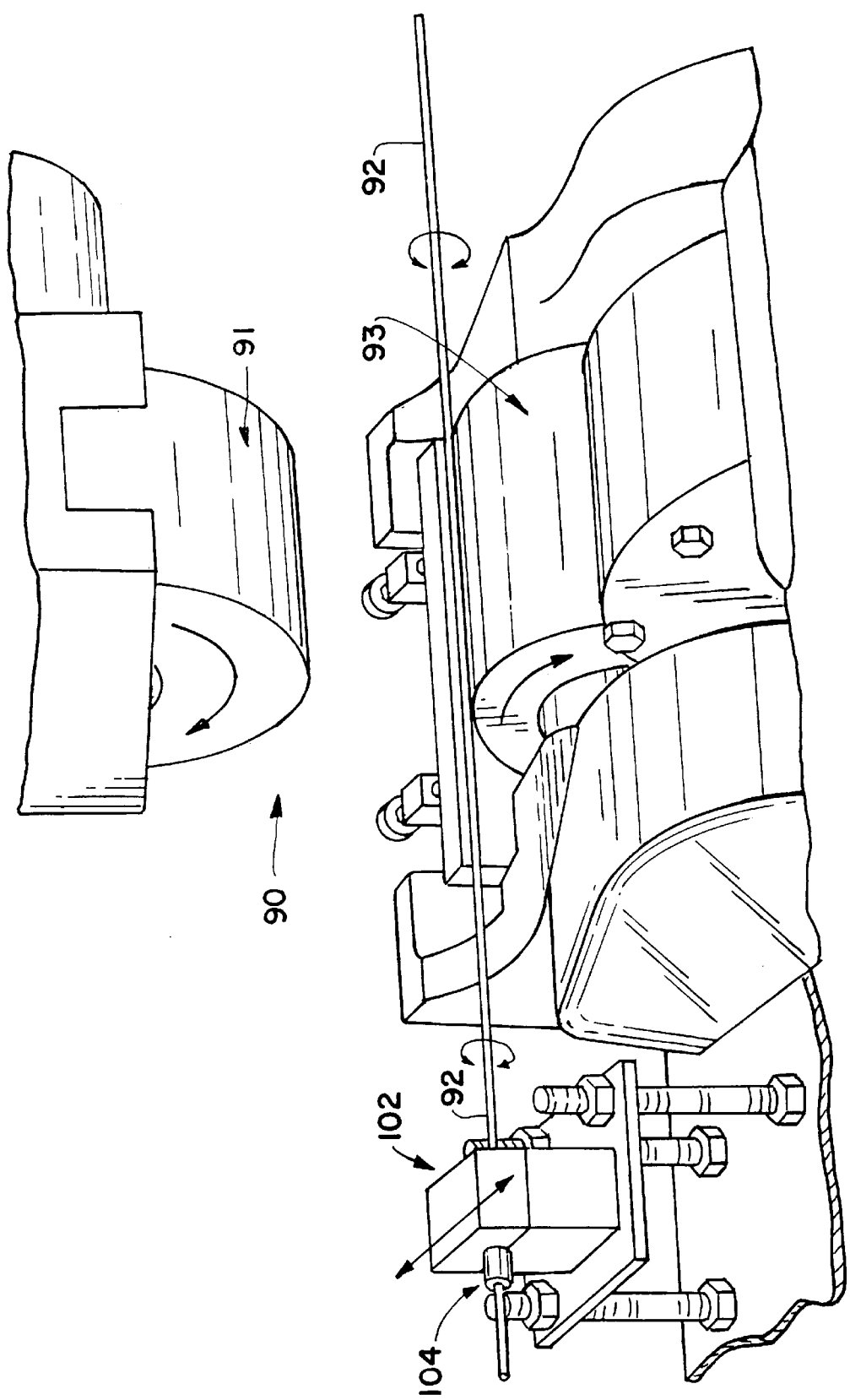
FIG. 5 is a somewhat diagrammatic view of grinding apparatus used for removing predetermined lengths of wire wrapping from the length of elastomeric tube; and, FIG. 6 is a pictorial view of the apparatus used for rotating the wire wrapped tube while the wrapping removal step is performed.
Figure 6:
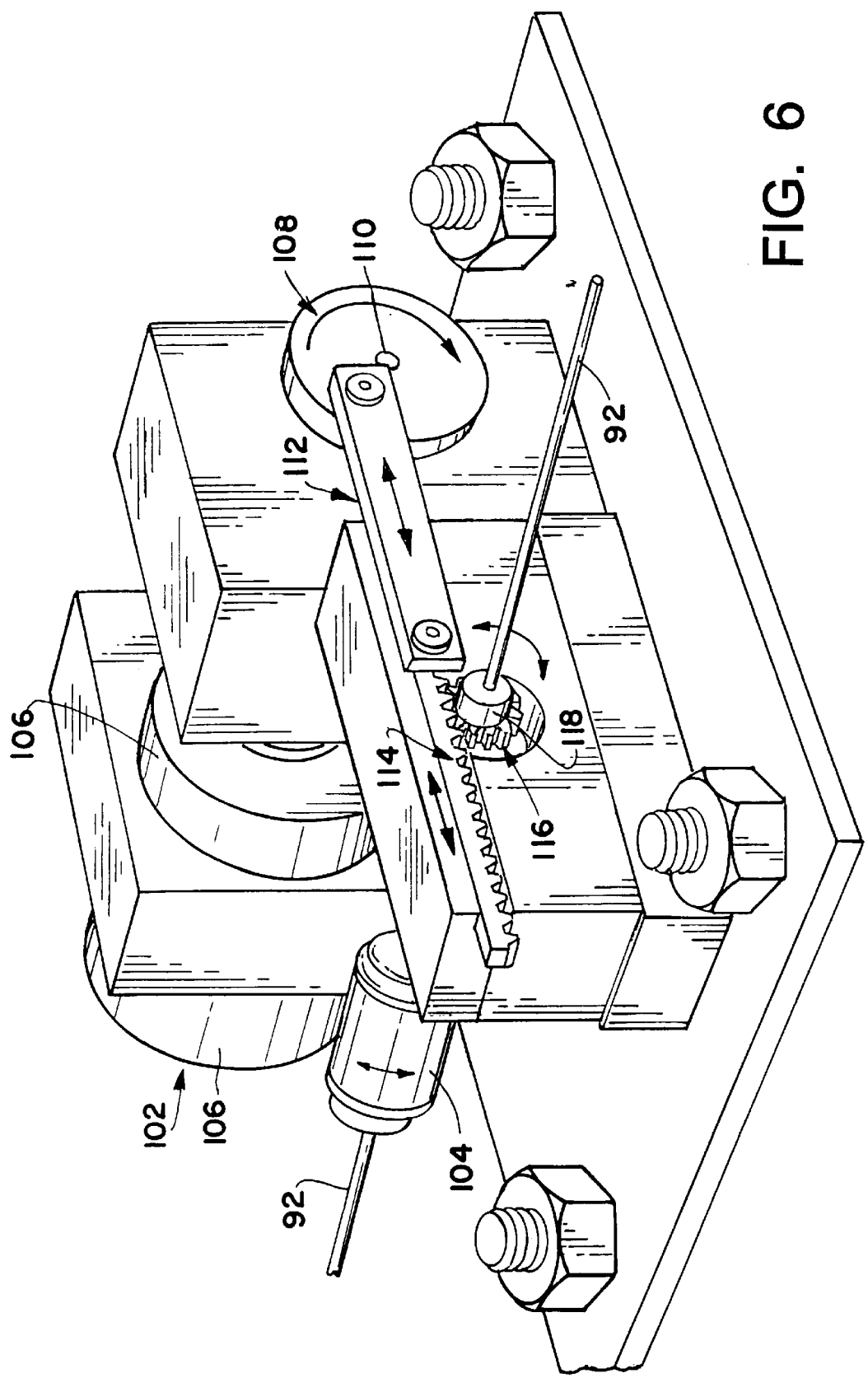

Referring in particular to FIGS. 5 and 6, my preferred form of grinding apparatus can be understood. Specifically, the grinder 90 is a centerless grinder modified by the addition of a motor driven clamping device 102 having a releasable collet 104 which firmly grips the wire braided stock at a point adjacent to where grinding is to begin and rotates, for example, 360° clockwise, then 360° counter-clockwise to expose the entire circumference of the wire braided area to be removed by the grinder. The grinder 90 includes an upper grinding wheel 91 and a support wheel 93 arranged to engage on opposite sides of the catheter stock 92 passing therebetween. The operation and control of the grinder is well known.

The device 102 (see FIG. 6) is driven by motor 106 with a crank arm 108 attached to an output shaft 110 of the motor. The crank arm 108 is connected with a connecting rod 112 that drives a rack gear 114 which rotates a pinion 116. The catheter stock 92 passes through the center of the pinion 116. The pinion is attached to a rotatably mounted shaft 118 that supports collet 104, which firmly grips the catheter stock 92 at a point adjacent to where grinding is to begin. As the rack gear 114 moves back and forth, a reciprocating back and forth motion of the collet is generated. A rate of about 200 RPM for shaft 118 has been found satisfactory.

Figure 4E:
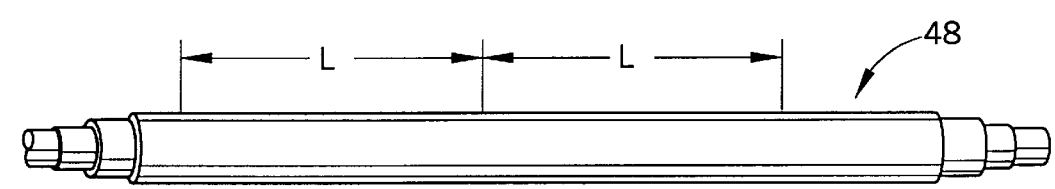
Figure 4F:
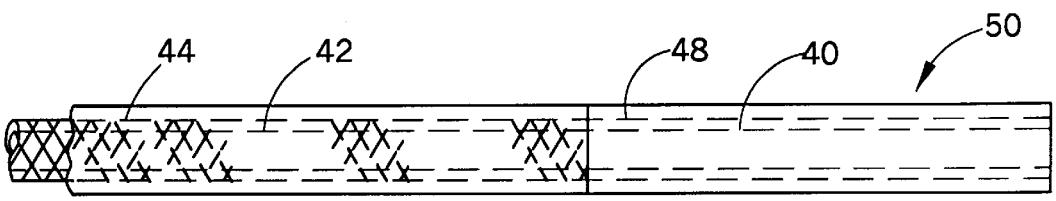
FIG. 4f is a view, partially in section, of a catheter formed in accordance with the present invention illustrating the internal construction of the catheter tip area.

After the braid has been removed in the desired areas, the braided and non-braided continuous section of stock is run through a plastic extruder and the finished coat of elastomer applied to a uniform diameter throughout the entire length of base stock resulting in the alternate sections of braid reinforced and non-braided sections being covered by an outer jacket 48 (FIG. 4*e*). Subsequently, the wire mandrel is removed. Thereafter, the entire length of catheter material is ground to have the desired final exterior catheter diameter with a proper surface smoothness. This is a known form of grinding using a centerless grinder. The catheter sections are cut to length which results in a main wire reinforced body and a 3½ inches non-reinforced tip portion. The tip portion 50 (FIG. 4*f*) can be subsequently tapered and/or shaped as desired. Additionally, thereafter, hub or other elements are added to the catheter body, as needed.

As can be seen, the described method can be varied widely. It is important to note, however, that the labor-intensive problems involved with attaching a separate tip to a wire braid reinforced catheter body are totally eliminated by the subject processing. Also, the discontinuous operation of laying multiple spaced apart circumferential epoxy bands onto the elastomeric tube has been eliminated. Additionally, grinding the joint between the tip and the body is eliminated. This elimination of the added steps and labor results in a less expensive catheter construction. In addition to reduced labor costs, the resulting catheter is significantly better because the possibility of failure at a bonded section are totally eliminated.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. A method of manufacturing multiple catheters from a continuous feedstock, the method comprising the steps of:
   providing an elongate first cylindrical tube;
   disposing multiple strands of wiring wrapping onto said elongate first cylindrical tube to form a first wire wrapped cylindrical tube;
   applying a contiguous bonding agent coating to the first wire wrapped cylindrical tube to form a first composite cylindrical tube, the continuous bonding agent coating bonding said multiple strands of wire wrapping to said elongate first cylindrical tube;

after applying the continuous bonding agent coating to the first wire wrapped cylindrical tube, removing predetermined sections of said wire wrapping from about said elongate first cylindrical tube to leave the first composite cylindrical tube with multiple wire wrapped sections spaced from one another by unwrapped sections;

coating said first composite cylindrical tube formed in the removing step with a predetermined thickness of a continuous finish coating; and, dividing said first composite cylindrical tube formed in the coating step into multiple catheters by cutting the first composite cylindrical tube at locations corresponding to said unwrapped sections.

2. The method of manufacturing multiple catheters according to claim 1 wherein the step of providing said elongate first cylindrical tube includes coating a one of a plastic and metal mandrel feed stock with a predetermined thickness of a first plastic material.

3. The method of manufacturing multiple catheters according to claim 1 wherein the step of disposing said multiple strands of wire wrapping onto said first elongate cylindrical tube includes braiding said multiple strands of wire wrapping about said first elongate first cylindrical tube.

4. The method of manufacturing multiple catheters according to claim 3 wherein the step of braiding said multiple strands of wire wrapping includes braiding sixteen strands of 0.003 inch stainless steel wire wrapping onto said first elongate first cylindrical tube.

5. The method of manufacturing multiple catheters according to claim 1 wherein the step of applying said continuous bonding agent coating to said first wire wrapped cylindrical tube includes coating said first wire wrapped cylindrical tube with a predetermined continuous thickness of a first plastic.

6. The method of manufacturing multiple catheters according to claim 1 wherein the step of removing predetermined sections of said wire wrapping includes grinding predetermined sections of said wire wrapping from about said elongate first cylindrical tube.

7. The method of manufacturing multiple catheters according to claim 6 wherein the step of grinding predetermined sections of said wire wrapping includes rotating a first portion of said continuous feedstock to be ground without rotating the remaining portion of the continuous feedstock.

8. The method of manufacturing multiple catheters according to claim 7 wherein the step of rotating said first portion of said continuous feedstock to be ground includes alternately rotating said first portion in clockwise and counterclockwise directions without rotating said remaining portion of the continuous feedstock.

9. The method of manufacturing multiple catheters according to claim 1 further including the step of forming predetermined contoured tips on ends of said multiple catheters by grinding end portions of said multiple catheters using a centerless grinder.

10. The method of manufacturing multiple catheters according to claim 9 further including the step of removing said mandrel feed stock from said elongate first cylindrical tube.

11. The method of manufacturing multiple catheters according to claim 1 where in the step of coating said first composite cylindrical tube includes coating said first composite cylindrical tube with a predetermined continuous thickness of a first elastomeric material.

12. The method of manufacturing multiple catheters according to claim 1 wherein:

the step of providing said elongate first cylindrical tube includes coating a one of a plastic and metal mandrel feed stock with a predetermined thickness of a first plastic material;

the step of disposing said multiple strands of wire wrapping onto said first elongate first cylindrical tube includes braiding said multiple strands of wire wrapping about said first elongate first cylindrical tube;

the step of applying said continuous bonding agent coating to said first wire wrapped cylindrical tube includes coating said first wire wrapped cylindrical tube with a predetermined continuous thickness of a first plastic;

the step of removing predetermined sections of said wire wrapping from about said elongate first cylindrical tube includes grinding predetermined sections of said wire wrapping from about said elongate first cylindrical tube to leave the first composite cylindrical tube with multiple wire wrapped sections spaced from one anther by unwrapped sections; and, the step of coating said first composite cylindrical tube includes coating said first composite cylindrical tube with a predetermined continuous thickness of a first elastomeric material.

13. The method of manufacturing multiple catheters according to claim 12 wherein each of said steps of coating a one of a plastic and metal mandrel, braiding said multiple strands of wire wrapping, coating said first wire wrapped cylindrical tube with a predetermined thickness of a first plastic, grinding predetermined sections of said wire wrapping, and coating said first composite cylindrical tube with a predetermined thickness of a first elastomeric material are performed sequentially.

14. The method of manufacturing multiple catheters according to claim 13 further including the step of forming predetermined contoured tips on ends of said multiple catheters by grinding end portions of said multiple catheters using a centerless grinder.

15. The method of manufacturing multiple catheters according to claim 14 further including the step of removing said mandrel feed stock from said elongate first cylindrical tube.

16. A method of manufacturing multiple catheters from a continuous feedstock, the method comprising the steps of:

providing an elongate first cylindrical tube;

disposing multiple strands of wire wrapping onto said elongate first cylindrical tube to form a first wire wrapped cylindrical tube;

applying to the first wire wrapped cylindrical tube a continuous bonding agent coating to form a first composite cylindrical tube, the continuous bonding agent coating bonding said multiple strands of wire wrapping to said elongate first cylindrical tube;

removing predetermined sections of said wire wrapping from about said elongate first cylindrical tube to leave the first composite cylindrical tube with multiple wire wrapped sections spaced from one another by unwrapped sections;

coating said first composite cylindrical tube formed in the removing step with a predetermined continuous thickness of a first elastomeric finish coating material; and, dividing said first composite cylindrical tube formed in the coating step into multiple catheters by cutting the first composite cylindrical tube at locations corresponding to said unwrapped sections.

17. The method of manufacturing multiple catheters according to claim 16 wherein the step of removing predetermined sections of said wire wrapping includes grinding predetermined sections of said wire wrapping from about said elongate first cylindrical tube while alternately rotating the predetermined sections in clockwise and counterclockwise directions without rotating said remaining portion of the elastomeric tube.

18. A method of manufacturing multiple catheters from a continuous feedstock, the method comprising the steps of:
- providing an elongate first cylindrical tube by coating a mandrel feed stock with a predetermined thickness of a first plastic material;
- disposing multiple strands of wire wrapping onto said first elongate first cylindrical tube by braiding said multiple strands of wire wrapping about said first elongate first cylindrical tube;
- applying a continuous bonding agent coating to said first wire wrapped cylindrical tube by coating said first wire wrapped cylindrical tube with a predetermined continuous thickness of a first plastic;
- removing predetermined sections of said wire wrapping from about said elongate first cylindrical tube by grinding predetermined sections of said wire wrapping from about said elongate first cylindrical tube to leave the first composite cylindrical tube with multiple wire wrapped sections spaced from one anther by unwrapped sections; and,
- coating said first composite cylindrical tube by coating said first composite cylindrical tube with a predetermined continuous thickness of a first elastomeric material.

19. The method of manufacturing multiple catheters according to claim 18 wherein each of said steps of coating a one of a plastic and metal mandrel, braiding said multiple strands of wire wrapping, coating said first wire wrapped cylindrical tube with a predetermined thickness of a first plastic, grinding predetermined sections of said wire wrapping, and coating said first composite cylindrical tube with a predetermined thickness of a first elastomeric material are performed sequentially.

20. The method of manufacturing multiple catheters according to claim 19 further including the step of forming predetermined contoured tips on ends of said multiple catheters by grinding end portions of said multiple catheters using a centerless grinder.

21. The method of manufacturing multiple catheters according to claim 20 further including the step of removing said mandrel feed stock from said elongate first cylindrical tube.

22. The method of manufacturing multiple catheters according to claim 18 wherein the step of removing predetermined sections of said wire wrapping includes grinding predetermined sections of said wire wrapping from about said elongate first cylindrical tube while alternately rotating the predetermined sections in clockwise and counterclockwise directions without rotating said remaining portion of the elastomeric tube.

23. A method of manufacturing angiographic catheters comprising:
a) forming a length of cylindrical elastomeric tube of a predetermined length;
b) braiding multiple strands of wire wrapping onto the entire length of said elastomeric tube;
c) extruding a bonding agent onto the wire wrapping for the entire length of said elastomeric tube to bond the strands of wire wrapping to each other and the elastomeric tube;
d) removing predetermined sections of the wire wrapping from about the elastomeric tube to leave said length of elastomeric tube with multiple wire wrapped sections spaced from one another by unwrapped sections;
e) coating a continuous outer layer of elastomer over said predetermined length of elastomeric tube with multiple wire wrapped sections spaced from one another by unwrapped sections; and,
f) thereafter, cutting the coated length of elastomeric tube with multiple wire wrapped sections spaced from one another by unwrapped sections transversely at locations selected to reduce said length to multiple pieces of coated wire wrapped sections each having a coated unwrapped section joined thereto on at least one end thereof.

24. The method as set forth in claim 23 wherein the wire wrapping removing in step (d) includes removing the wire wrapping by grinding.

25. The method as set forth in claim 24 wherein the step of removing the wire wrapping by grinding includes rotating a first portion of said elastomeric tube to be ground without rotating the remaining portion of the elastomeric tube.

26. The method as set forth in claim 25 wherein the step of rotating said first portion of the elastomeric tube includes alternately rotating said first portion in clockwise and counterclockwise directions without rotating said remaining portion of the elastomeric tube.

27. The method as set forth in claim 23 wherein the coating step (e) includes extruding said continuous outer layer of elastomer over said predetermined length of elastomeric tube.

28. The method as set forth in claim 23 wherein the forming step (a) includes extruding a first plastic material over a wire or plastic mandrel to form said length of cylindrical elastomeric tube.

29. The method as set forth in claim 23 wherein the step of extruding said bonding agent onto said wire wrapping includes the step of extruding a plastic material onto said wire wrapping.

30. The method as set forth in claim 29 wherein:
- the step of forming said length of cylindrical elastomeric tube includes by extruding a first plastic material over a wire or plastic mandrel; and
- the step of extruding said bonding agent onto said wire wrapping includes extruding a second plastic material onto said wire wrapping.

31. The method as set forth in claim 30 wherein the steps of extruding said first plastic material and said second plastic material include extruding a urethane material.

32. A method of manufacturing angiographic catheters comprising:
a) providing a length of plastic tube of a predetermined length and braiding multiple strands of wire wrapper thereabout;
b) applying a plastic bonding agent to the wire wrapping for the entire said length to bond the strands of wire wrapping to each other and to said plastic tube;
c) after applying the plastic bonding agent to the wire wrapping, grinding away the wire wrapping at predetermined spaced locations along the length of the elastomeric tube to provide a series of wire wrapped sections joined by non-wrapped sections;
d) coating a plastic coating over both the wire wrapped sections and the non-wrapped sections throughout the length thereof; and,
e) thereafter, severing the coated length into pieces with the pieces each constituting a wire wrapped section with a non-wrapped section joined to at least one end thereof.

33. The method asset forth in claim 32 wherein the plastic bonding agent step (b) includes extruding the plastic bonding agent onto said wire wrapping.

34. The method as set forth in claim 32 where the grinding step (c) includes rotating a first portion of said length of plastic tube to be ground without rotating the remaining portion of the length of plastic tube.

35. The method as set forth in claim 34 wherein the rotating step includes alternately rotating said first portion in clockwise and counterclockwise directions without rotating said remaining portion of the length of plastic tube.

36. A method of manufacturing angiographic catheters comprising:

providing a length of plastic tube of a predetermined length and braiding multiple strands of wire wrapper thereabout;

applying a plastic bonding agent to the wire wrapping for the entire said length to bond the strands of wire wrapping to each other and to said plastic tube;

after applying the plastic bonding agent to the wire wrapping, grinding away the wire wrapping at predetermined spaced locations along the length of the elastomeric tube by rotating a first portion of said continuous feedstock to be ground alternately in clockwise and counterclockwise directions without rotating the remaining portion of the continuous feedstock to provide a series of wire wrapped sections joined by non-wrapped sections;

coating a plastic coating over both the wire wrapped sections and the non-wrapped sections throughout the length thereof; and, thereafter, severing the coated length into pieces with the pieces each constituting a wire wrapped section with a non-wrapped section joined to at least one end thereof.

37. The method of manufacturing angiographic catheters according to claim 36 wherein the step of rotating the first portion of the continuous feedstock alternately in clockwise and counterclockwise direction includes rotating the first portion of the continuous feedstock alternately at least 360° clockwise and 360° counterclockwise.

38. The method of manufacturing angiographic catheters according to claim 37 wherein the step of rotating the first portion of the continuous feedstock alternately at least 360° clockwise and 360° counterclockwise includes rotating the first portion of the continuous feedstock alternately at least 360° clockwise and 360° counterclockwise at a rate of substantially 200 cycles per minute.

* * * * *